United States Patent
Tal et al.

(10) Patent No.: US 11,504,499 B2
(45) Date of Patent: *Nov. 22, 2022

(54) CATHETER INSERTION APPARATUS

(71) Applicant: Covidien AG, Neuhausen Am Rheinfall (CH)

(72) Inventors: Michael G. Tal, Woodbridge, CT (US); Brett Haarala, Framingham, MA (US); Christopher V. Rainieri, Erie, CO (US); Richard Braga, North Easton, MA (US)

(73) Assignee: COVIDIEN AG, Neuhausen am Rheinfall (CH)

(*) Notice: Subject to any disclaimer, the term of this patent is extended or adjusted under 35 U.S.C. 154(b) by 254 days.

This patent is subject to a terminal disclaimer.

(21) Appl. No.: 16/854,945

(22) Filed: Apr. 22, 2020

(65) Prior Publication Data

US 2020/0246587 A1 Aug. 6, 2020

Related U.S. Application Data

(60) Division of application No. 15/880,012, filed on Jan. 25, 2018, now Pat. No. 10,668,248, which is a (Continued)

(51) Int. Cl.
*A61M 25/00* (2006.01)
*A61M 1/36* (2006.01)
*A61M 25/01* (2006.01)

(52) U.S. Cl.
CPC ...... *A61M 25/0068* (2013.01); *A61M 1/3661* (2014.02); *A61M 25/008* (2013.01); (Continued)

(58) Field of Classification Search
CPC .......... A61M 25/0068; A61M 25/0102; A61M 25/008; A61M 25/0071; A61M 2025/0037; A61M 25/0069

See application file for complete search history.

(56) References Cited

U.S. PATENT DOCUMENTS 701,075 A 5/1902 McCully
2,541,691 A 2/1951 Eicher
(Continued)

FOREIGN PATENT DOCUMENTS

CA 2389227 10/2001
EP 0107810 5/1984
(Continued)

OTHER PUBLICATIONS

International Search Report and Written Opinion of International Application No. PCT/US2005/40101, dated Feb. 9, 2007, 4 pp.
(Continued)

*Primary Examiner* — Bradley J Osinski

(74) *Attorney, Agent, or Firm* — Shumaker & Sieffert, P.A.

(57) ABSTRACT

A catheter is provided including a first lumen and a second lumen. A first member is disposed for relative movement within the first lumen and defines a cavity. A second member is disposed for relative movement within the second lumen. The cavity of the first member is configured for disposal of the second member. The catheter may include an elongated tubular body that includes the first lumen and the second lumen. The first member may have a distal portion that extends beyond the distal end of the body. The distal portion may include the cavity. The cavity may be defined by a member lumen. The first and second members may include tubular stylettes. The second member may include a guidewire.

24 Claims, 12 Drawing Sheets

Related U.S. Application Data continuation of application No. 11/266,319, filed on Nov. 4, 2005, now Pat. No. 9,913,962.

(60) Provisional application No. 60/625,005, filed on Nov. 4, 2004.

(52) U.S. Cl.
CPC .... *A61M 25/0071* (2013.01); *A61M 25/0102* (2013.01); *A61M 25/0069* (2013.01); *A61M 2025/0031* (2013.01); *A61M 2025/0037* (2013.01)

(56) References Cited

U.S. PATENT DOCUMENTS

| | | |
|---|---|---|
| D208,838 S | 10/1967 | St. Amand |
| 4,134,402 A | 1/1979 | Mahurkar |
| D254,270 S | 2/1980 | Ziegler |
| 4,306,562 A | 12/1981 | Osborne |
| D272,651 S | 2/1984 | Mahurkar |
| 4,443,333 A | 4/1984 | Mahurkar |
| 4,568,329 A | 2/1986 | Mahurkar |
| 4,583,968 A | 4/1986 | Mahurkar |
| 4,601,697 A | 7/1986 | Mammolenti et al. |
| 4,604,379 A | 8/1986 | Twardowski et al. |
| D289,682 S | 5/1987 | Dragan |
| 4,675,004 A | 6/1987 | Hadford et al. |
| 4,682,978 A | 7/1987 | Martin |
| 4,687,471 A | 8/1987 | Twardowski et al. |
| 4,692,141 A | 9/1987 | Mahurkar |
| D292,825 S | 11/1987 | Dragan |
| 4,770,652 A | 9/1988 | Mahurkar |
| 4,772,269 A | 9/1988 | Twardowski et al. |
| D298,461 S | 11/1988 | Manno |
| 4,798,193 A | 1/1989 | Giesy et al. |
| 4,808,155 A | 2/1989 | Mahurkar |
| 4,824,435 A | 4/1989 | Giesy et al. |
| 4,842,582 A | 6/1989 | Mahurkar |
| 4,850,358 A | 7/1989 | Millar |
| 4,883,426 A | 11/1989 | Ferrer |
| 4,894,057 A | 1/1990 | Howes |
| 4,895,561 A | 1/1990 | Mahurkar |
| 4,904,238 A | 2/1990 | Williams |
| D312,872 S | 12/1990 | Mahl |
| 4,988,356 A | 1/1991 | Crittenden et al. |
| 5,009,636 A | 4/1991 | Wortley et al. |
| 5,015,184 A | 5/1991 | Perry et al. |
| 5,167,623 A | 12/1992 | Cianci et al. |
| 5,171,227 A | 12/1992 | Twardowski et al. |
| 5,197,951 A | 3/1993 | Mahurkar |
| 5,209,723 A | 5/1993 | Twardowski et al. |
| 5,221,255 A | 6/1993 | Mahurkar |
| 5,221,256 A | 6/1993 | Mahurkar |
| 5,273,527 A | 12/1993 | Schatz et al. |
| 5,281,134 A | 1/1994 | Schultz |
| 5,282,788 A | 2/1994 | Wilk et al. |
| 5,290,282 A | 3/1994 | Casscells |
| 5,318,518 A | 6/1994 | Plechinger et al. |
| 5,318,527 A | 6/1994 | Hyde et al. |
| 5,320,605 A | 6/1994 | Sahota |
| 5,336,165 A | 8/1994 | Twardowski |
| 5,336,184 A | 8/1994 | Teirstein |
| 5,374,245 A | 12/1994 | Mahurkar |
| 5,378,230 A | 1/1995 | Mahurkar |
| 5,395,332 A | 3/1995 | Ressemann et al. |
| 5,403,291 A | 4/1995 | Abrahamson |
| 5,405,320 A | 4/1995 | Twardowski |
| 5,405,341 A | 4/1995 | Martin |
| 5,419,777 A | 5/1995 | Holling |
| 5,443,457 A | 8/1995 | Ginn et al. |
| 5,451,216 A | 9/1995 | Quinn |
| 5,458,584 A | 10/1995 | Ginn et al. |
| 5,464,398 A | 11/1995 | Haindl |
| 5,484,397 A | 1/1996 | Twardowski |
| 5,486,159 A | 1/1996 | Mahurkar |
| 5,509,897 A | 4/1996 | Twardowski et al. |
| 5,536,234 A | 7/1996 | Newman |
| 5,549,541 A | 8/1996 | Muller |
| 5,554,136 A | 9/1996 | Luther |
| 5,562,640 A | 10/1996 | McCabe et al. |
| 5,569,182 A | 10/1996 | Twardowski et al. |
| 5,571,087 A | 11/1996 | Ressemann et al. |
| 5,571,093 A | 11/1996 | Cruz et al. |
| 5,607,440 A | 3/1997 | Danks et al. |
| 5,685,867 A | 11/1997 | Twardowski et al. |
| 5,707,351 A | 1/1998 | Dorsey, III |
| 5,725,495 A | 3/1998 | Strukel et al. |
| 5,776,092 A | 7/1998 | Farin et al. |
| 5,782,797 A | 7/1998 | Schweich, Jr. et al. |
| 5,785,678 A | 7/1998 | Griep et al. |
| 5,788,680 A | 8/1998 | Linder |
| 5,788,681 A | 8/1998 | Weaver et al. |
| 5,801,012 A | 9/1998 | Soff et al. |
| 5,830,196 A | 11/1998 | Hicks |
| 5,858,009 A | 1/1999 | Jonkman |
| 5,902,476 A | 5/1999 | Twardowski |
| 5,961,486 A | 10/1999 | Twardowski et al. |
| 6,059,748 A | 5/2000 | Teirstein et al. |
| 6,063,099 A | 5/2000 | Danks et al. |
| 6,086,565 A | 7/2000 | Ouchi |
| 6,126,631 A | 10/2000 | Loggie |
| 6,129,738 A | 10/2000 | Lashinski et al. |
| 6,132,456 A | 10/2000 | Sommer et al. |
| 6,132,616 A | 10/2000 | Twardowski et al. |
| 6,146,536 A | 11/2000 | Twardowski |
| 6,152,910 A | 11/2000 | Agro et al. |
| 6,190,357 B1 | 2/2001 | Ferrari et al. |
| 6,299,444 B1 | 10/2001 | Cohen |
| 6,409,700 B1 | 6/2002 | Siegel, Jr. et al. |
| 6,423,050 B1 | 7/2002 | Twardowski |
| 6,428,502 B1 | 8/2002 | Lang |
| 6,576,609 B1 | 6/2003 | Soff et al. |
| 6,592,565 B2 | 7/2003 | Twardowski |
| 6,916,313 B2 | 7/2005 | Cunningham |
| 7,141,035 B2 | 11/2006 | Haggstrom |
| 7,182,746 B2 | 2/2007 | Haarala et al. |
| 2002/0016564 A1 | 2/2002 | Courtney et al. |
| 2002/0065492 A1 | 5/2002 | McGuckin, Jr. et al. |
| 2003/0013985 A1 | 1/2003 | Saadat |
| 2004/0059298 A1 | 3/2004 | Sanderson |
| 2004/0193046 A1 | 9/2004 | Nash et al. |
| 2004/0243095 A1 | 12/2004 | Nimkar et al. |
| 2005/0131449 A1 | 6/2005 | Salahieh et al. |
| 2008/0082079 A1 | 4/2008 | Braga et al. |
| 2010/0168718 A1 | 7/2010 | Bellisario et al. |

FOREIGN PATENT DOCUMENTS

| | | |
|---|---|---|
| EP | 0341721 | 11/1989 |
| EP | 0555780 | 8/1993 |
| EP | 0623356 | 11/1994 |
| EP | 0965311 | 12/1999 |
| FR | 2326941 | 10/1976 |
| GB | 2028136 | 3/1980 |
| JP | 08103492 | 4/1996 |
| JP | H-08308933 | 11/1996 |
| WO | 92/14500 | 9/1992 |
| WO | 94/28961 | 12/1994 |
| WO | 95/10317 | 4/1995 |
| WO | 99/38550 | 8/1999 |

OTHER PUBLICATIONS

International Preliminary Report on Patentability from International Application No. PCT/US2005/040101, dated May 3, 2007, 4 pp.
Prosecution History from counterpart Canadian Application No. 2593731 dated Aug. 21, 2007 through Jan. 16, 2014, 71 pp.
Prosecution History from counterpart European Application No. 0585136.3, now European Patent No. 1814610, dated Feb. 4, 2011 through Apr. 9, 2020, 141 pp.
Prosecution History from U.S. Appl. No. 11/266,319, dated Jul. 29, 2009 through Feb. 8, 2018, 184 pp.

(56) References Cited

OTHER PUBLICATIONS

Prosecution History from U.S. Appl. No. 15/880,012, dated Jan. 26, 2018 through Jan. 23, 2020, 27 pp.

CATHETER INSERTION APPARATUS

CROSS-REFERENCE TO RELATED APPLICATIONS

This application is a divisional of U.S. patent application Ser. No. 15/880,012 filed Jan. 25, 2018, which is a continuation of U.S. patent application Ser. No. 11/266,319, filed on Nov. 4, 2005, now U.S. Pat. No. 9,913,962, which claims benefit of and priority to U.S. Provisional Application No. 60/625,005, filed Nov. 4, 2004, the disclosure of each of which is hereby incorporated by reference in its entirety.

BACKGROUND OF THE INVENTION

Technical Field of the Invention

The present disclosure relates generally to medical catheter apparatus, and more particularly to a catheter insertion apparatus.

Description of the Related Art

Catheters are known medical devices for administration of fluids within cavities, ducts, and vessels of a body. Various known catheter devices have been employed for simultaneous withdrawal and introduction of a fluid within a body. These devices may utilize multiple lumens, such as dual lumen catheters that facilitate bi-directional fluid flow whereby one lumen performs withdrawal of blood and the other lumen introduces treated blood to the vessel. In hemodialysis applications catheters are used to withdraw blood from a blood vessel and return the treated blood back to the blood vessel after the blood is treated by an artificial kidney device.

Methods of catheter placement in a body vessel are well known. Current catheter placement techniques may result in tearing or snagging of vessel tissue as well as patient discomfort during placement. To address such trauma, catheters are often manufactured from softer and more flexible materials. These softer and more flexible materials may require the use of a stiffener to aid in the placement of the catheter in the vessel.

Therefore, it would be desirable to have a catheter apparatus that facilitates placement within a body vessel with reduced vessel trauma and patient discomfort. It would highly desirable if the catheter apparatus and its constituent parts are easily and efficiently manufactured and assembled.

SUMMARY OF THE INVENTION

Accordingly, a catheter apparatus is provided that facilitates placement within a body vessel with reduced vessel trauma and patient discomfort to overcome the disadvantages and drawbacks of the prior art. Most desirably, the catheter apparatus is easily and efficiently manufactured and assembled.

In one particular embodiment, a catheter is provided, in accordance with the principles of the present disclosure. The catheter includes a first lumen and a second lumen. A first member is disposed for relative movement within the first lumen and defines a cavity. A second member is disposed for relative movement within the second lumen. The cavity of the first member is configured for disposal of the second member.

In an alternate embodiment, the catheter has an elongated tubular body defining a first lumen and a second lumen. The first member extends within the first lumen and is slidably movable relative thereto. The first member includes a distal portion that extends beyond a distal end of the body. The distal portion of the first member defines a member lumen. A second member extends within the second lumen and is slidably movable relative thereto. The second member extends beyond the distal end of the body. A wire extends through the second member and the member lumen such that the first member and the second member extend from the distal end of the body in a configuration for passage through a body vessel.

In an exemplary embodiment, the distal tip of the catheter is tapered. In another exemplary embodiment, the distal tip of the catheter is comprised of a material having a durometer greater than the durometer of the body of the catheter. In another exemplary embodiment, the distal tip of the catheter comprises at least one rounded edge at a surface of the distal tip so that the surface is smoother than it would be in the absence of the rounded edge. In another exemplary embodiment, the first and second members are comprised of a first tubular stylette and a second tubular stylette, respectively, wherein the first stylette has an outer diameter substantially equivalent to the inner diameter of the first lumen and the second stylette has an outer diameter substantially equivalent to the inner diameter of the second lumen. In yet another exemplary embodiment, the first and second members are comprised of a first and second tubular stylette, respectively, wherein at least one of the first and second stylettes has an inner diameter that is smaller than the outer diameter of a guidewire to be inserted into the stylette and is able to expand when the guidewire is inserted into the stylette so that the inner diameter of the stylette expands to accommodate the guidewire when the guidewire is inserted into the stylette and contracts when the guidewire is withdrawn from the stylette.

In another exemplary embodiment a hemodialysis catheter includes an elongated tubular body including a distal end and defining a first lumen, a second lumen and a septum disposed therebetween. A first tubular stylette extends within the first lumen and is slidably movable relative thereto. The first stylette includes a distal portion that extends beyond a distal end of the body. The distal portion of the first member defines a member lumen. A second tubular stylette extends within the second lumen and is slidably movable relative thereto. The second stylette extends beyond the distal end of the body. A guidewire extends through the tubular stylette and the member lumen such that the first member and the second member extend from the distal end of the body in a tapered configuration for guiding the catheter through a body vessel.

A method for inserting a catheter within a vessel of a body is provided. The method includes the steps of; disposing a guidewire within the body vessel, the guidewire having a proximal end and a distal end; providing a catheter including a first lumen and a second lumen; providing a first member being disposed for relative movement within the first lumen and defining a cavity, a second member being disposed for relative movement within the second lumen and including the guidewire; inserting the proximal end of the guidewire through the cavity of the first member; inserting the proximal end of the guidewire, passed through the cavity of the first member, into a distal end of the second member; and passing the proximal end of the guidewire through the second member to a proximal end thereof such that a distal end of the catheter is disposed at a location within the body vessel.

In another exemplary embodiment a catheter includes a first lumen and a second lumen. A first member is disposed for relative movement within the first lumen and defines a member lumen. A second member is disposed for relative movement within the second lumen. The member lumen of the first member is configured for disposal of the second member.

In another exemplary embodiment a catheter includes an elongated tubular body defining a first lumen and a second lumen. A first member extends within the first lumen and is slidably movable relative thereto. The first member includes a distal portion that extends beyond a distal end of the body. The distal portion of the first member defines a member lumen. A wire extends through the second lumen and the member lumen such that the first member extends from the distal end of the body in a configuration for passage through a body vessel.

In another exemplary embodiment, a hemodialysis catheter includes an elongated tubular body including a distal end and defining a first lumen: a second lumen and a septum disposed therebetween. A first tubular stylette extends within the first lumen and is slidably movable relative thereto. The first stylette includes a distal portion that extends beyond a distal end of the body. The distal portion of the first member defines a member lumen. A guidewire extends through the second lumen and the member lumen such that the first member extends from the distal end of the body in a tapered configuration for guiding the catheter through a body vessel.

In yet another exemplary embodiment, a catheter includes an elongated tubular body defining a first lumen, second lumen and third lumen. A first member extends within the first lumen and is slidably movable relative thereto. The first lumen includes a distal portion that extends beyond a distal end of the body. The distal portion of the first member defines a member lumen. A second member extends within the second lumen and is slidably movable relative thereto. The second member extends beyond the distal end of the body. A wire extends within the third lumen and is slidably movable relative thereto. The wire extends through the second member and member lumen so that the first member and second member extend from the distal end of the body in a configuration for passage through a body vessel.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may foe best understood by reference to the following description, taken in connection with the accompanying drawings, as set forth below.

DETAILED DESCRIPTION OF THE EXEMPLARY EMBODIMENTS

The exemplary embodiments of the catheter and methods of use disclosed are discussed in terms of medical catheters for the administration of fluids of a subject and more particularly, in terms of a catheter that facilitates placement within a body vessel. The catheter is advantageously configured to reduce trauma and prevent patient complications. It is envisioned that the present disclosure may be employed with a range of catheters, such as, for example, hemodialysis, peritoneal, infusion, PICC, CVC, port, biliary, urethral, in any acute and/or chronic catheter application.

In the discussion that follows, the term "proximal" will refer to the portion of a structure that is closer to a practitioner, while the term "distal" will refer to the portion that is further from the practitioner. As used herein, the term "subject" refers to a human patent or other animal. According to the present disclosure, the term "practitioner" refers to a doctor, nurse or other care provider and may include support personnel.

The following discussion includes a description of the catheter, in accordance with the principles of the present disclosure. Reference will now be made in detail to the exemplary embodiments of the disclosure, which are illustrated in the accompanying figures.

Figure 1:
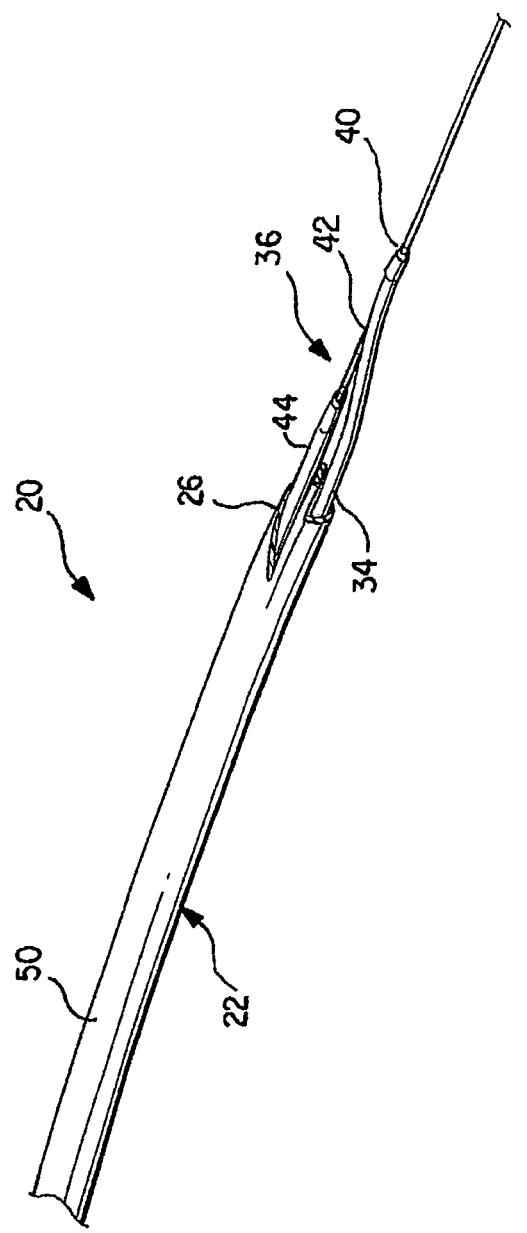
FIG. 1 is a cutaway perspective view of a catheter in accordance with the principles of the present disclosure.
Figure 2:
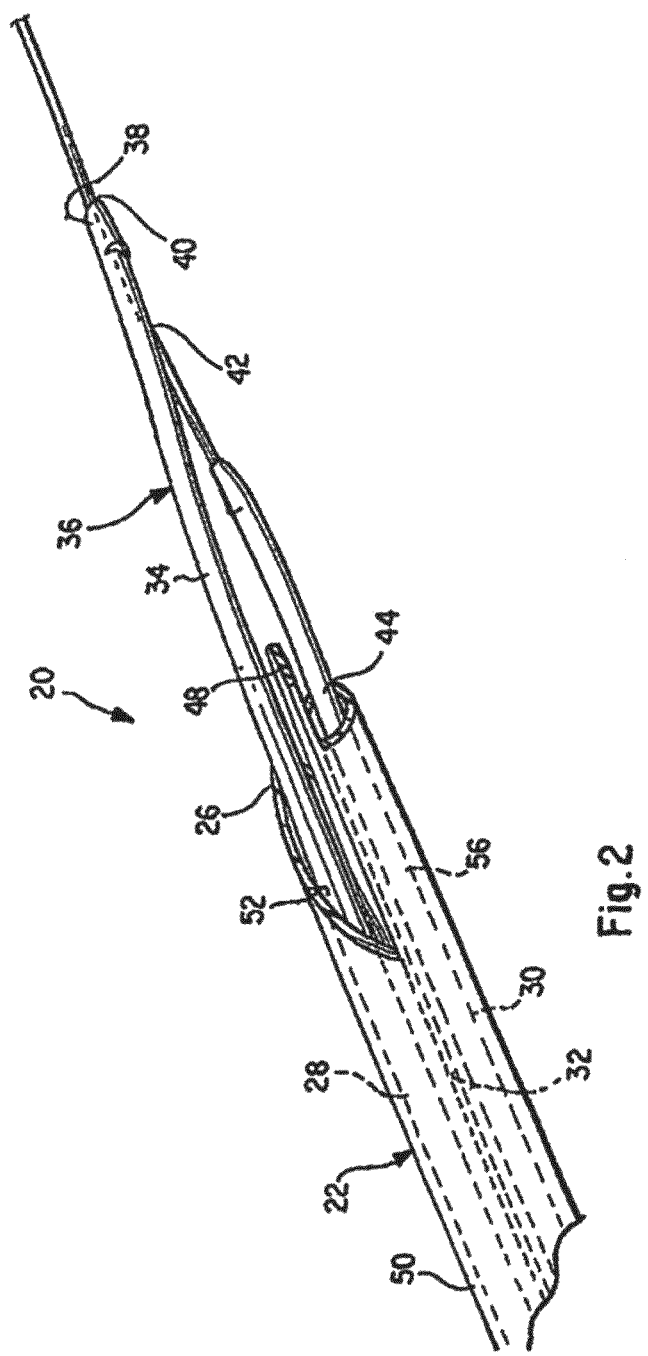
FIG. 2 is an enlarged cutaway perspective view of the catheter shown in FIG. 1.

Turning now to the figures, wherein like components are designated by like reference numerals throughout the several views. Referring initially to FIGS. 1 and 2, a catheter 20 includes an elongated tubular body 22 including a proximal end 24 (FIG. 5) and a distal end 26. Body 22 defines a first lumen 28, a second lumen 30 and a septum 32 disposed therebetween (all shown in phantom in FIG. 2). It is contemplated that distal end 26 may have various configurations, such as, for example, tapered and symmetrical. It is further contemplated that body 22 may be variously dimensioned including length and diameter, such as, for example, 13-15 French.

A first member, such as, for example, first tubular stylette 34 extends within first lumen 28 and is slidably movable relative thereto. It is contemplated that first stylette 34 may have varying degrees of rigidity or stiffness. First stylette 34 includes a distal portion 36 that extends beyond distal end 26. It is contemplated that the first member may be tubular, solid, have a tubular portion, have a solid portion, combinations thereof and the like, etc.

Distal portion 36 defines a cavity, such as, for example, member lumen 38 (shown in phantom in FIG. 2). Member lumen 38 includes a distal opening 40 and a proximal opening 42. Member lumen 38 is configured for slidable movement of a guidewire 46 therein to facilitate passage of catheter 20 to a desired location within a body vessel (not shown). It is envisioned that member lumen 38 may have various configurations, such as, for example, cylindrical, rectangular, elliptical, polygonal, combinations thereof and the like, etc. Member lumen 38 may be configured for movement of various structures therein, in various directions and orientations, according to the requirements of a particular catheter application. It is contemplated that the cavity may include a loop or hole.

A second member includes, for example, second tubular stylette 44 (shown clearly in FIGS. 6-9) which extends within second lumen 30 and is slidably movable relative thereto. Second stylette 44 has a distal portion 47 (shown clearly in FIGS. 6-9) that extends beyond distal end 26. It is contemplated that second stylette 44 may have varying degrees of rigidity or stiffness. When disposed within lumens 28, 30, distal portion 36 of first stylette 34 extends beyond distal portion 47 of second stylette 44 such that distal portions 36, 47 are offset. It is contemplated that stylettes 34, 44 may be of alternative lengths. Stylettes 34, 44 are employed within body 22 to provide stiffening of distal end 26 and tapering of catheter 20. Stylettes 34, 44 are also configured to maintain integrity after placement. This configuration of catheter 20 advantageously forms a transition to facilitate placement of catheter 20 within a body vessel (not shown) thereby reducing trauma and preventing patient complications. It is contemplated that the second member may fee tubular, solid, may have tubular portion, have a solid portion, combinations thereof and the like, etc.

Figure 3:
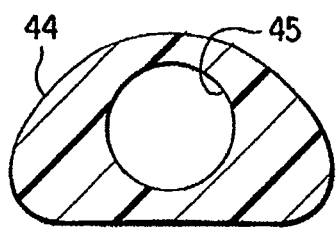
FIG. 3 is an enlarged cross section view of a second member of the catheter shown in FIG. 1.
Figure 4:
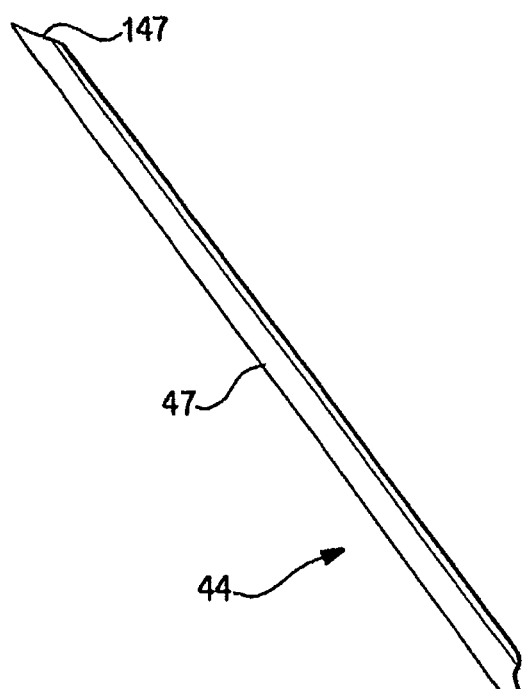
FIG. 4 is a cutaway plan view of an alternate embodiment of a distal end of the second member shown in FIG. 1.

The second member includes a guidewire 46 that is configured to extend through second stylette 44 and member lumen 38 such that first stylette 34 and second stylette 44 extend from distal end 26 in a tapered configuration for guiding catheter 20 through a body vessel. It is contemplated that the second member may not include guidewire 46 and that guidewire 46 is a separate component of catheter 20. Guidewire 46 is of sufficient rigidity to support body 22 during placement and may have a smooth outer surface. It is envisioned that guidewire 46 may have a lubricious coating. Suitable lubricious coatings include, for example, hydrophilic coating, polytetrafluoroethylene (PTFE), silicone oil, other biocompatible lubricant, combinations thereof and the like. Guide wire 46 may be of various lengths to extend into the heart and beyond body 22. Catheter 20 may also include a guidewire outer sheath (not shown), disposed for positioning within lumen 30 and over guidewire 46. The guidewire outer sheath enhances stiffening and facilitates passage of body 22 through a subcutaneous tract Second stylette 44 is elongated and has a substantially D-shaped or semi-circular cross-section, as shown in FIG. 3. Second stylette 44 defines a passage 45 configured for slidable movement of guidewire 48 therein. Passage 45 may have various cross-sectional configurations, such as, for example, oval, rectangular, elliptical, polygonal, combinations thereof and the like. It is contemplated that first stylette 34 has a substantially D-shaped or semi-circular cross-section. It is further contemplated that the outer surfaces of stylettes 34, 44 may have various cross-sectional configurations, such as, for example, oval, rectangular, elliptical, polygonal, combinations thereof and the like. The outer surfaces of stylettes 34, 44 may conform to the inner surfaces of lumens 28, 30 to advantageously decrease friction and facilitate transition during placement of distal end 26. Stylettes 34, 44 may or may not be of uniform configuration with the inner surface of lumens 28, 30. In an alternate embodiment, as shown in FIG. 4, distal portion 47 of second stylette 44 has an angled tip 147 to provide a transition with first stylette 34. It is contemplated that tip 147 may be received by proximal opening 42 of member lumen 38.

Distal end 26 of body 22 includes a septum extension 48 that extends distally beyond first lumen 28 and second lumen 30. Septum extension 48 extends to prevent occlusion of first lumen 28 and second lumen 30 during use. It is envisioned that distal end 26 may not include an extension, and alternatively lumens 28, 30 may be in longitudinal alignment or staggered, it is further envisioned that lumens 28, 30, adjacent distal end 26, may include a spiral configuration.

Body 22 has a cylindrical outer surface 50. It is contemplated that body 22 may be variously dimensioned and attachable to other medical devices. It is further contemplated that outer surface 50 may have various cross-sectional configurations, such as, for example, oval, rectangular, elliptical, polygonal, combinations thereof and the like. Body 22 may also include lateral openings.

Lumens 28, 30 each have a substantially D-shaped or semi-circular cross-section. Lumens 28, 30 are elongated with body 22 and are configured to facilitate fluid flow. It is contemplated that lumens 28,30 may be configured for arterial and/or venous flow. It is envisioned that lumens 28, 30 may have various configurations, such as, for example, cylindrical, rectangular, elliptical, polygonal, combinations thereof and the like. Lumens 28, 30 may toe-configured for various forms of fluid flow in various directions and orientations, according to the requirements of a particular catheter application.

Lumens 28, 30 may be uniformly dimensioned or include alternative dimensional cross sections within body 22, such as, narrow and broad portions, converging surfaces, undulating surfaces, combinations thereof and the like, etc. according to the particular flow indications and/or flow rate requirements. It is contemplated lumen 28 and lumen 30 may extend alternative lengths. It is further contemplated that body 22 may include one or a plurality of lumens, such as, for example, a triple lumen configuration, similar to that discussed below with regard to FIGS. 10-12.

First lumen 28 includes an inlet opening 62 that is disposed adjacent to distal end 26 of body 22. An outlet opening 54 (FIG. 5) of first lumen 28 is disposed adjacent a proximal end 24 of body 22. Inlet opening 52 may be variously dimensioned and configured, such as, for example, rectangular, elliptical, polygonal, combinations thereof and the like, and may include adapters, clips, etc. to facilitate fluid flow and/or attachment to other structure. Second lumen 30 includes an outlet opening 56 (shown in phantom in FIG. 2) that is disposed adjacent to distal end 26. An inlet opening 58 (FIG. 5) of second lumen 30 is disposed adjacent proximal end 24. Outlet opening 56 may foe variously dimensioned and configured, such as, for example, rectangular, elliptical, polygonal, combinations thereof and the like, etc. and may include adapters, clips, etc. to facilitate fluid flow and/or attachment to other structure.

The components of catheter 20 are fabricated from materials suitable for medical applications, such as, for example, polymerics or metals, such as stainless steel, combinations thereof and the like depending on the particular catheter application and/or preference of a practitioner. Semi-rigid and rigid polymerics such as, for example, polyvinylchloride (PVC) and polycarbonate (PC) are contemplated for fabrication, as well as resilient materials, such as molded medical-grade polypropylene, thermoplastic urethanes, or polyethylene. For example, stylettes 34, 44 may be made from polytetrafluoroethylene, polyethylene, other materials having similar durometer range and low friction properties, combinations thereof and the like. Stylettes 34, 44 can be compatible with a standard uncoated coil guidewire for cost efficiency, as well as other coated guidewires and coils. Stylettes 34, 44 may include a hydrophilic coating, polytetrafluoroethylene (PTFE), silicone oil or other biocompatible lubricant, combinations thereof and the like on part or all of the components to enhance insertion in catheter 20, tissue and a body lumen, as well as removal after catheter placement. Proximal end 24 of catheter 20 may have a luer adapter or threaded adapter. Catheter 20 may be color coded to match various components. Alternatively, a valve adapter (not shown) is attachable to proximal end 24. The valve adapter may be integral with catheter 20. Proximal end may include structure that allows guidewire 46 to be fixed in position relative to stylette 44, such as, for example, a pinch clamp or Tuohy-borst adapter, to prevent guidewire 46 from unintentionally moving in or out of the vessel during insertion. One skilled in the art, however, will realize that other materials and fabrication methods suitable for assembly and manufacture, in accordance with the present disclosure, also would be appropriate.

The components of catheter 20, as shown in FIGS. 5-9, similar to that described, are assembled, sterilized and packaged for use. In operation, catheter 20 is prepared for disposal within a body vessel (not shown) in contemplation of a hemodialysis for a subject. Initially, a hollow needle cannula (not shown) is inserted into the body vessel. It is contemplated that the needle cannula creates a venotomy or entry site within the subject for body vessel access. The needle cannula may be disposed within the skin of the subject, adjacent the neck and clavicle, for accessing a vein. Guidewire 46 is inserted through a proximal end of the needle cannula and tunneled through to a desired location within the body vessel. The needle cannula is removed leaving guidewire 46 disposed within the body vessel and having a proximal end of guidewire 46 extending from the body vessel to the exterior of the subject. It is envisioned that in particular applications the skin may be nicked on either side of guidewire 46 with a scalpel (not shown) so that a subcutaneous vessel entry site can be pre-dilated. It is further envisioned that a dilator may be fed with guidewire 46 into a venotomy site to pre-dilate the entry site.

A tunneler (not shown) is attached to distal end 26 and inserted through an exit site in contemplation of forming a subcutaneous tract. It is envisioned that the exit site may be disposed adjacent to the chest wall below a venotomy site. The tunneler tunnels a subcutaneous tract from the exit site to the venotomy site. The tunneler is attached to distal end 26 such that the tunneler draws distal end 26 through the subcutaneous tract to the venotomy site. Body 22 is pulled through the venotomy site. The tunneler is removed from distal end 26. It is envisioned that the tunneler may include a sheath to enclose the mating connection with distal end 26. The sheath may also prevent trauma to the subject during passage through the subcutaneous tract.

Figure 5:
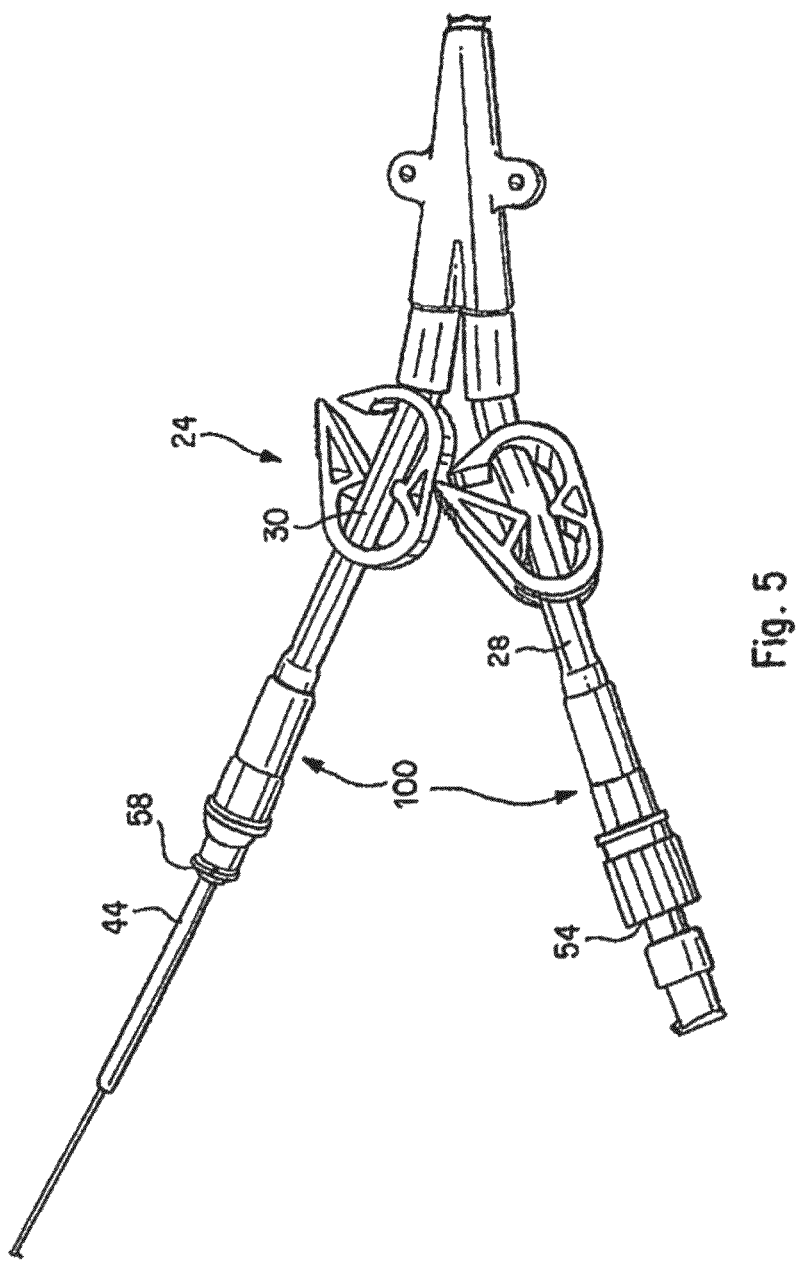
FIG. 5 is a cutaway perspective view of a proximal end of the catheter shown in FIG. 1.
Figure 6:
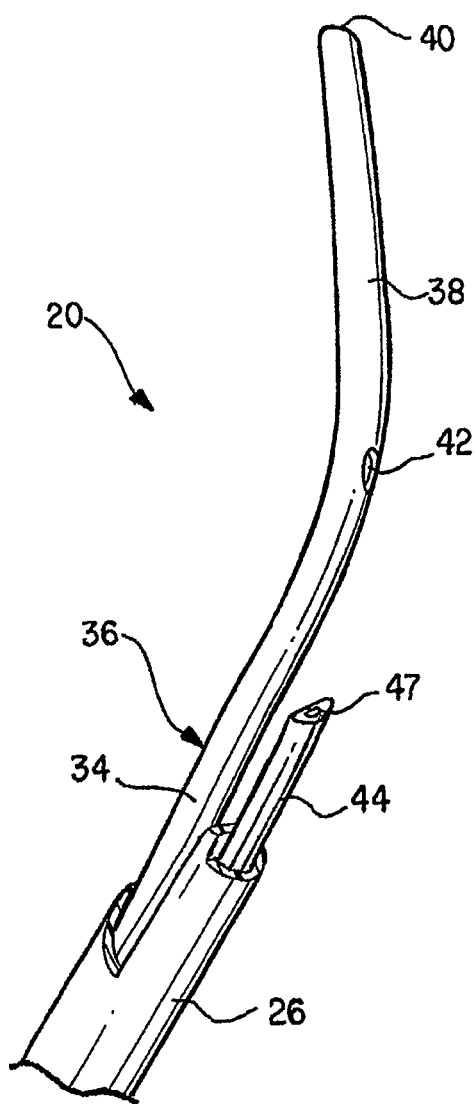
FIG. 6 is a cutaway perspective view of a distal end of the catheter shown in FIG. 1.

Stylettes 34, 44 are assembled with lumens 28, 30, via insertion with openings 54, 58, respectively and shown in FIG. 5. Stylettes 34, 44 are advanced distally through lumens 28, 30 and extend distally beyond distal end 26 of body 22, as shown in FIG. 6. It is anticipated that stylettes 34, 44 may be threaded onto adapters 100, as shown in FIG. 5. Distal portion 36 of first stylette 34 extends beyond distal portion 47 of second stylette 44. First stylette 34 is longer than second stylette 44. It is envisioned that first stylette 34 and second stylette 44 may be inserted in lumens 28, 30, respectively, prior to insertion of stylettes 34, 44 within the vessel or assembled after insertion, by the practitioner.

Figure 7:
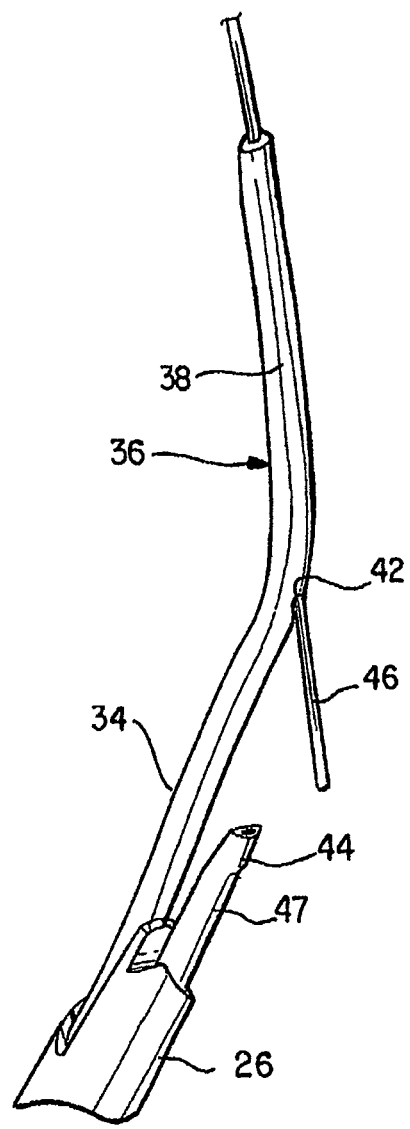
FIG. 7 is a cutaway perspective view of the distal end of the catheter shown in FIG. 1.
Figure 8:
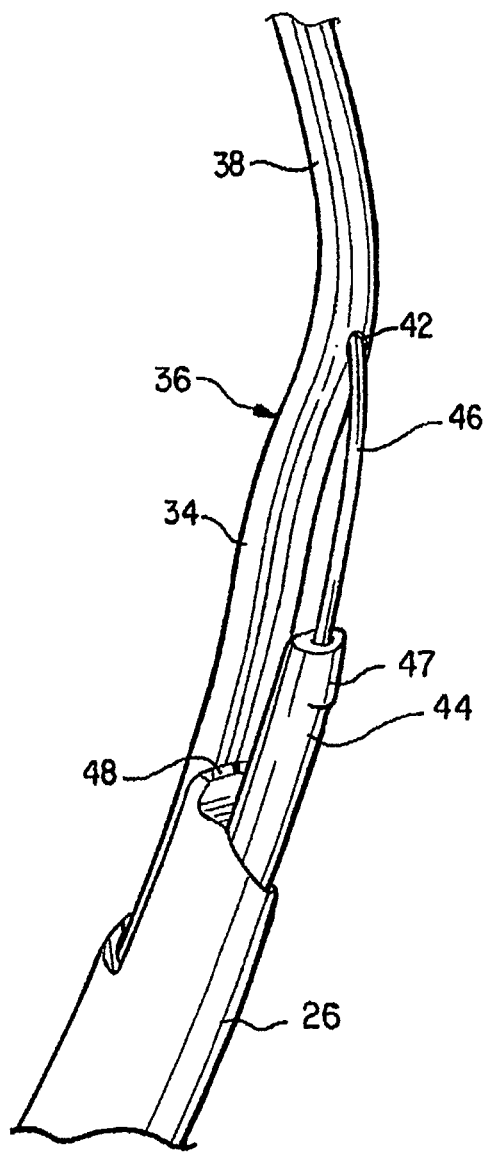
FIG. 8 is a cutaway perspective view of the distal end of the catheter shown in FIG. 1.
Figure 9:
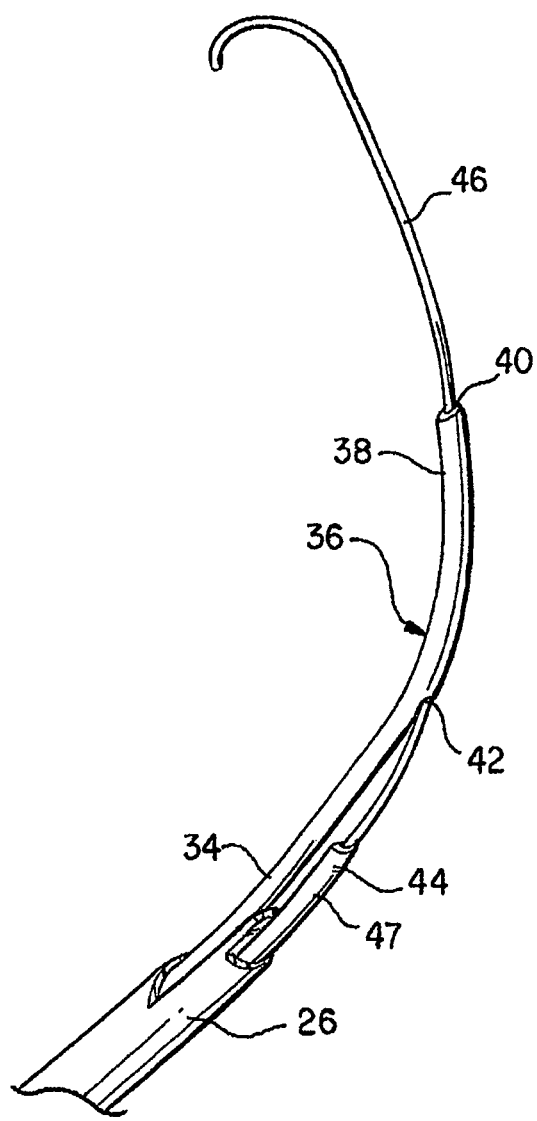
FIG. 9 is a cutaway perspective view of the distal end of the catheter shown in FIG. 1.

The proximal end of guidewire 46, disposed within the body vessel, is received by distal opening 40 of member lumen 38, as shown in FIG. 7. First stylette 34 is manipulated distally such that the proximal end of guidewire 46 exits proximal opening 42 of member lumen 38. The proximal end of guidewire 46 is manipulated for insertion with distal portion 47 of second stylette 44, as shown in FIG. 8. Guidewire 46 is continuously fed through member lumen 38 and passage 45 of second stylette 44 such that stylettes 34, 44 are placed distally within the body vessel to a desired location (not shown). Stylettes 34, 44 are continuously fed through lumens 28, 30 of catheter 20 such that lumens 28, 30 are placed distally within the body vessel to a desired location. Guidewire 46 and stylettes 34, 44 may be removed from the body vessel and catheter 20. Catheter 20 may be maintained in position. Lumens 28, 30 may be flushed with fluid.

Guidewire 46 extends through second stylette 44 and member lumen 38 such that first stylette 34 and second stylette 44 extend from distal end 26 of body 22 in a tapered configuration for guiding catheter 20 through the body vessel. The above-described procedure for disposal of catheter 20 within a body vessel may be used for Seldinger procedures, tunneling, reverse tunneling, and other related procedures. It is contemplated that prior to insertion of guidewire 46 into first stylette 34, catheter 20 may be tunneled through subcutaneous skin to a position on the chest or neck of the subject, according to the requirements of a particular application.

Upon placement of catheter 20 at a desired location within a body vessel, it is envisioned that catheter 20 may be employed for administration of fluids within the body of a subject in procedures alternate to hemodialysis. Catheter 20 and other exemplary catheters described herein may be employed for: double-lumen catheter exchange over a single wire; direct placement of a catheter through a tunnel; dialysis catheters, tunneled and acute non-tunneled; chronic tunneled infusion catheters, such as Hickman catheters; acute infusion catheters, such as triple lumen central venous catheters; and various multi-lumen catheters.

Operation of catheter 20 and other exemplary catheters described herein may benefit from several advantages including; efficiency, instead of using two wires for tunneled dialysis catheter exchange, catheter 20 may be used over a single wire; safety, catheter 20 reduces trauma to the venotomy by providing a smooth tapering to the catheter tip and is occlusive to reduce the likelihood of air embolization through the lumens; and patient comfort and safety, catheters 20 may be composed from softer materials that are more comfortable to the patient and less traumatic. Catheter 20 eliminates the use of a peel away catheter along with the associated risk of air embolization. Further, catheter 20 is cost-effective by eliminating the need for a second guidewire and peel-away structure, as well as reducing the time required for a procedure. Catheter 20 can also reduce the need for multiple dilatation, making the procedure easier and faster.

Figure 10:
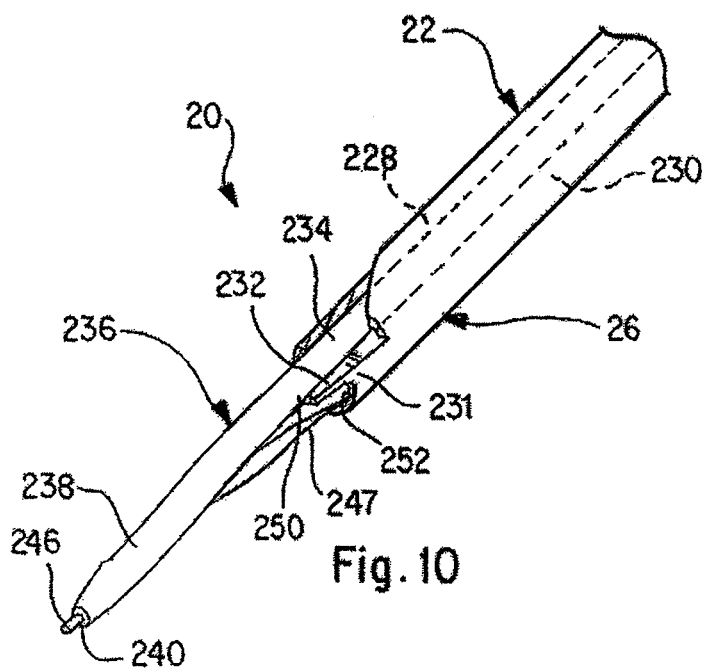
FIG. 10 is a cutaway perspective view of an alternate embodiment of the catheter shown in FIG. 1.
Figure 11:
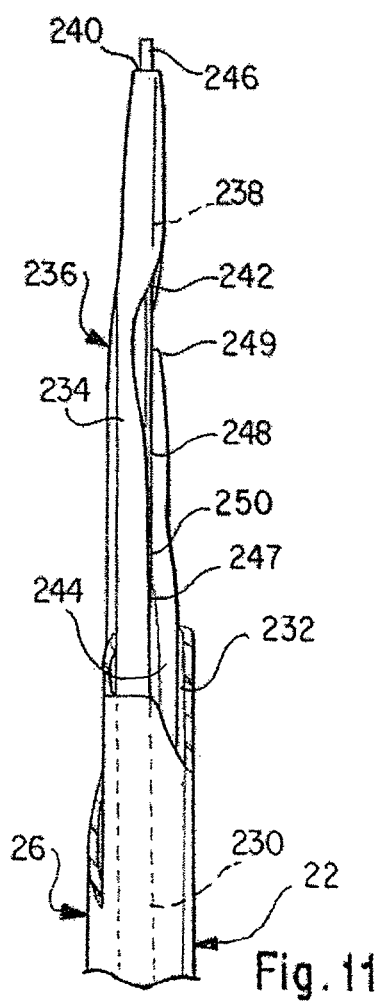
FIG. 11 is a cutaway plan view of a distal end of the catheter shown in FIG. 10.
Figure 12:
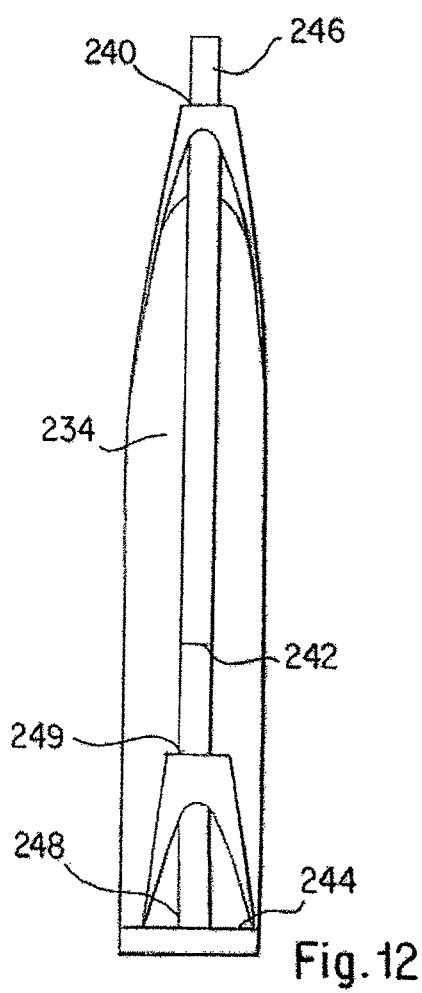
FIG. 12 is an enlarged cutaway plan view of the distal end of the catheter shown in FIG. 10.

Referring to FIGS. 10-12, in an alternate embodiment, catheter 20, similar to that described with regard to FIGS. 1-9, has a triple lumen configuration. Body 22 defines a first lumen 228, a second lumen 230 (similar to lumens 28, 30 described above) and a third lumen 231 (the phantom lead line portions identifying the inner lumen). A septum 232 is disposed between first lumen 228 and second lumen 230, and is connected to the portion of body 22 that defines third lumen 231.

A first tubular stylette 234 extends with first lumen 228 and is slidably movable relative thereto. First stylette 234 includes a distal portion 236 that extends beyond distal end 26. Distal portion 236 defines a member lumen 238 that includes a distal opening 240 and a proximal opening 242. Member lumen 238 is configured for slidable movement of a guidewire 246 therein to facilitate passage of catheter 20 to a desired location within a body vessel (not shown).

Guidewire 246 extends with third lumen 231 and is slidably movable relative thereto. Guidewire 246 may be fixed within third lumen 231. Lumen 231 has a substantially circular cross-section, however, may be D-shaped or semi-circular depending on the requirements of a particular application. It is envisioned that lumen 231 may have various configurations, such as, for example, cylindrical, rectangular, elliptical, polygonal, combinations thereof and the like. Guidewire 246 may be configured to extend with any of the lumens of body 22.

Lumen 231 may be uniformly dimensioned or include alternative dimensional cross sections within body 22, such as, narrow and broad portions, converging surfaces, undulating surfaces, combinations thereof and the like, etc. Lumen 231 includes an inlet opening 252 disposed adjacent to distal end 26 of body 22. An outlet opening (not shown) of lumen 231 is disposed adjacent a proximal end 24 of body 22.

A second tubular stylette 244 extends within second lumen 230 and is slidably movable relative thereto. Second stylette 244 has a distal portion 247 that extends beyond distal end 26. Distal portion 247 defines a member lumen 248 that includes a distal opening 249 and a proximal opening 250. Member lumen 248 is configured for slidable movement of guidewire 246 therein to facilitate passage of catheter 20 to a desired location within a body vessel. When disposed within lumens 228, 230, distal portion 236 of first stylette 234 extends beyond distal portion 247 of second stylette 244 such that distal portions 236, 247 are offset. Stylettes 234, 244 are employed with body 22 to provide stiffening of distal end 26 and tapering of catheter 20. This configuration of catheter 20 advantageously forms a transition to facilitate placement of catheter 20 within a body vessel (not shown) thereby reducing trauma and preventing patient complications.

Guidewire 246 is configured to extend through member lumens 238,248 such that first stylette 234 and second stylette 244 extend from body vessel. Stylettes 234, 244 are assembled with lumens 228, 230 and advanced distally to extend beyond distal end 26 of body 22. Distal portion 236 of first stylette 234 extends beyond distal portion 247 of second stylette 244.

The proximal end of guidewire 246 is received by distal opening 240 of member lumen 238. First stylette 234 is manipulated distally such that the proximal end of guidewire 246 exits proximal opening 242 of member lumen 238. The proximal end of guidewire 246 is manipulated for insertion with distal portion 247 of second stylette 244. Distal opening 249 receives guidewire 246. Second stylette 244 is manipulated distally such that the proximal end of guidewire 246 exits proximal opening 250. Guidewire 246 is fed through member lumens 238, 248 into third lumen 231. Guidewire 246 is continuously fed through member lumens 238, 248 and third lumen 231 such that stylettes 234, 244 may be placed distally within the body vessel to a desired location.

Guidewire 246 extends through member lumens 238, 248 and third lumen 231 such that first stylette 234 and second stylette 244 extend from distal end 26 of body 22 in a tapered configuration for guiding catheter 20 through the body vessel. Catheter 20 may be used for Seldinger procedures, tunneling, reverse tunneling, and other related procedures. This configuration advantageously decreases vessel trauma and may reduce air embolism.

Figure 13A:
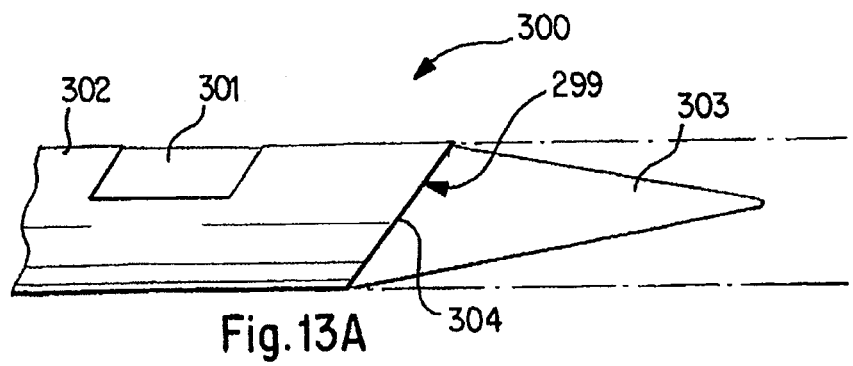
FIGS. 13A and 13B are enlarged perspective views of exemplary catheters.

In exemplary embodiments, a catheter can include a tapered distal tip to provide enhanced tracking and/or insertion of the catheter into tissue tracks and/or body vessels. To provide a tapered tip, the cross-sectional area of the distal tip region of the catheter may be reduced. The reduction in cross-sectional area may also decrease the size of the catheter lumens. In order to avoid any unacceptable reduction of flow that may result, the tapered distal tip cars include at least one of a spiral cut opening and slots. Tapering of the distal tip can be achieved by re-forming the distal tip of the catheter and/or the addition of a tapered tip structure and secure bonding, heat sealing, and/or welding of the tip structure to the catheter body using, for example, one or more suitable adhesives such as, for example, adhesives selected from the group consisting of a silicone adhesive, a cyanoacrylate adhesive, an acrylic adhesive, and epoxy adhesive, a polyurethane adhesive, combinations thereof and the like Re-forming of the catheter tip can be achieved using any suitable method including, for example, a heat re-forming method, a mechanical re-forming method, a chemical re-forming method, combinations thereof, and the like. An exemplary tapered catheter 300 is depicted in FIG. 13A. The catheter 300 includes a slot 301 in the catheter body 302 and a tapered distal tip 303. The catheter 300 in FIG. 13A also includes a spiral out opening 304 to facilitate fluid flow through the lumen 299. Thus, when compared to a non-tapered catheter such as catheter 305 depicted in FIG. 13B having a blunt tip 308, the catheter 300 may have a reduced cross-sectional area at the distal tip region due to the tapered configuration of tip 303. The catheter 300 having the tapered tip 303 may, however, provide superior tracking and/or Insertion of the catheter 300 into tissue tracks and/or body vessels compared to the blunt-tipped catheter 305.

Tapering of the distal tip, in addition to providing an improved profile for insertion and passage through tissue may allow for a closer fit on stylettes, or a guidewire, used for tracking and reinforcement of the catheter.

Figure 13B:
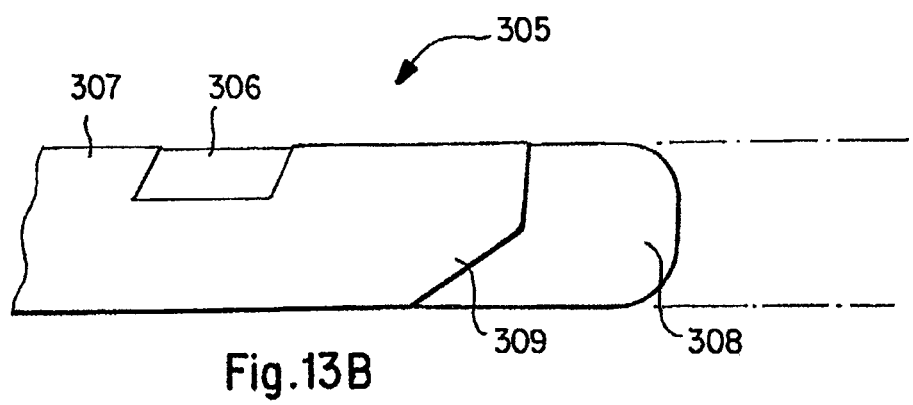

The catheter 300 in FIG. 13A also includes a spiral out 304 having a spiral pitch that is greater than the pitch of spiral cut 309 of catheter 305 depicted in FIG. 13B. Because the pitch of cut 304 is greater than the pitch of cut 309 of catheter 305, insertion of catheter 300 may be further enhanced compared to catheter 305.

Enhanced insertion may also be achieved by providing a distal tip region comprised of a material having a durometer greater than the durometer of the catheter body. For example, while the catheter body 302 or 307 may remain fairly flexible having a lower respective durometer, the tip region of the catheter 300 or 305 can be harder and less flexible thereby enhancing insertion and passage of the distal tip 303 or 308 through tissue.

Figure 14:
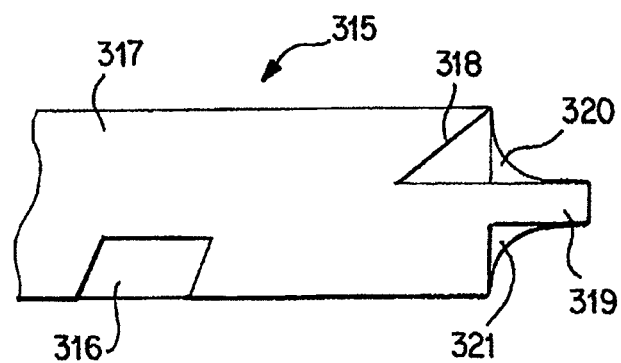
FIG. 14 is an enlarged perspective view of another exemplary catheter.

Another exemplary embodiment of a catheter 315 is depicted in FIG. 14. Catheter 315 includes a slot 316 in the catheter body 317 and spiral out opening 318. The catheter 315 also includes a longitudinally extending septum 319. To enhance insertion of the catheter 315, the catheter 315 further includes fillets or rounded edges 320 and 321 at the distal end of the catheter proximal to the spiral cut opening 318 and the septum 319. The rounded edges 320 and 321 substantially reduce or eliminate sharp edges at the distal end of the catheter 315 thereby creating surfaces that are smoother than they would have been in the absence of the rounded edges 320 and 321. The rounded edges 320 and 321 may significantly improve insertion of the catheter 315 by reducing drag. Although the catheter depicted in FIG. 14 includes two rounded edges, exemplary embodiments can include one more fillets and/or rounded edges at any location on the catheter where a fillet or rounded edge may reduce drag to improve insertion.

Figure 15:
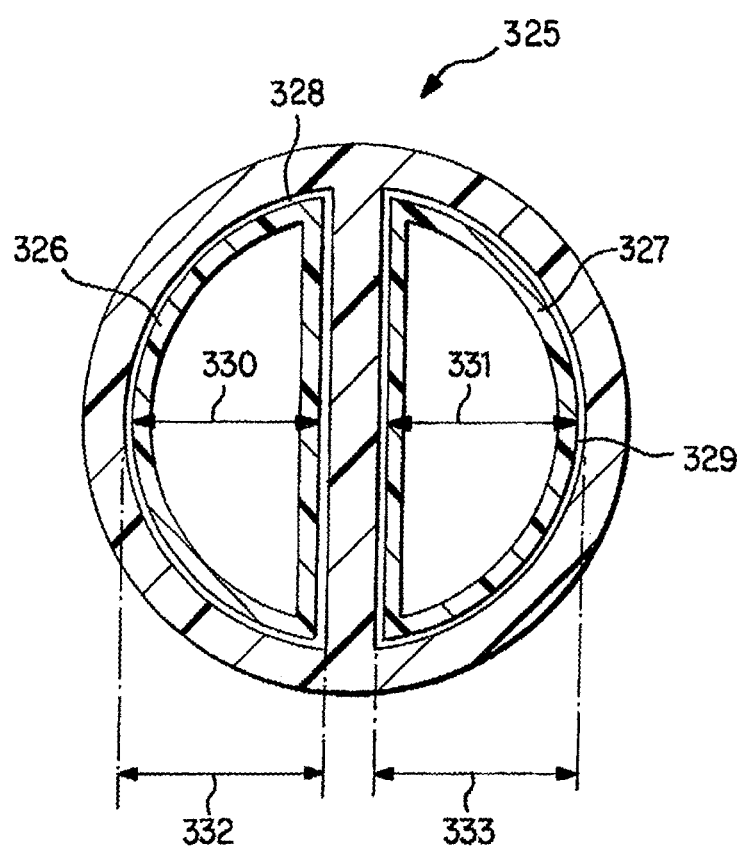
FIG. 15 is a cross-sectional view of an exemplary catheter and tubular stylettes.

Another exemplary embodiment is depicted in FIG. 15. Catheter 325 includes first and second stylettes for insertion and relative movement with respect to a first and second lumen in the catheter 325. The stylettes 326, 327 may be provided with an outer diameter 330, 331 that is substantially equivalent to the inner diameter 332, 333 of the lumens 328, 329. By providing stylettes 326, 327 with outer diameters 330, 331 that are substantially equivalent to the inner diameter 332, 333 of the lumens 328, 329, the ability to advance the catheter 325 may be enhanced by substantially reducing space between the exterior surface of the stylettes 326, 327 and the interior surface of the lumens 328, 329, which may otherwise catch the distal tip of a catheter on tissue. In addition, by increasing the size of the stylettes, stiffness of the catheter may also be increased. Catheter stiffness may also be improved by increasing the wall thickness of the stylettes.

Figure 16:
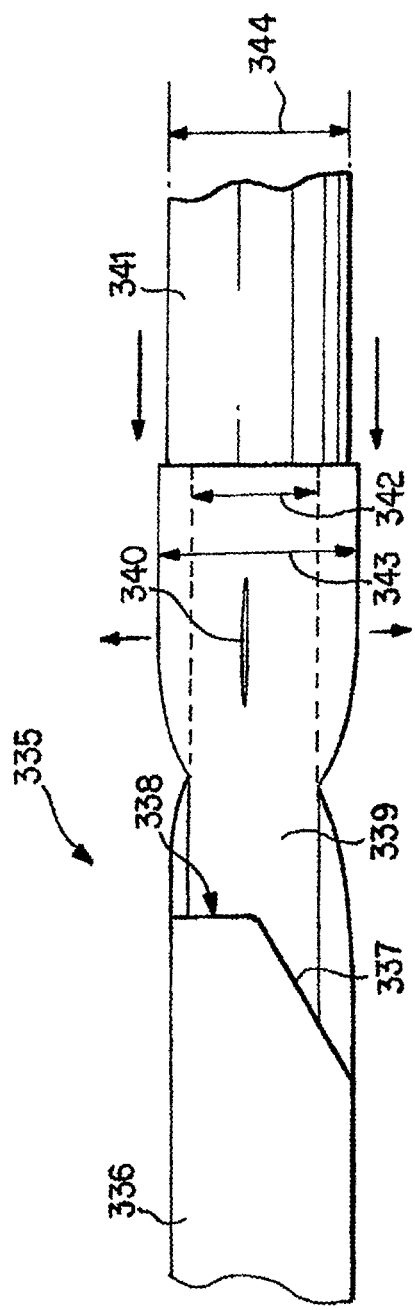
FIG. 16 is an enlarged perspective view of an exemplary catheter and tubular stylette.

Another exemplary embodiment of a catheter 335 is depicted in FIG. 18. Catheter 335 includes a catheter body 338 and a spiral cut 337 at a distal lumen opening 338. A stylette 339 having a normal inner diameter 342 is inserted into the distal lumen opening 338. The tubular stylette 339 is configured so that sis normal inner diameter 342 is smaller than the outer diameter 344 of a guidewire 341 to be inserted into the tubular stylette 339. The tubular stylette 339 is configured to expand so that its normal, inner diameter 342 expands to accommodate the guidewire 341 when the guidewire is inserted into the stylette 339 and contracts when the guidewire 341 is withdrawn from the tubular stylette 339. In an exemplary embodiment, the tubular stylette 339 can include a slit 340 in the body of the tubular stylette 339 to permit the desired expansion and contraction during insertion and withdrawal of the guidewire 341. Alternatively, it is possible that the tubular stylette 339 could be made of a flexible material or otherwise configured to permit expansion and contraction during insertion and withdrawal of the guidewire 341, instead of or in addition to silt 340. In addition, while stylette 339 depicted in FIG. 16 includes a single slit 340, exemplary embodiments may include 2, 3, 4 or more slits to achieve the desired expansion and contraction. In its expanded state, the inner diameter of the stylette 339 may increase to an expanded inner diameter 343 to accommodate the outer diameter 344 of the guidewire 341. When the guidewire 341 is inserted into the tubular stylette 339 and the inner diameter 342 is expanded as depicted, insertion of the catheter 335 is enhanced because the tubular stylette 339 acts as a dilator for the distal tip of the catheter. Expansion of the stylette can also be achieved using an assembly wherein the stylette and guidewire are integral and move relative to one another to expand and contract the stylette. Expansion of the stylette may also be achieved by increasing the outer diameter of the guidewire instead of providing a stylette having an expandable, inner diameter. Expansion of the stylette may also be achieved using a balloon inflated with a fluid such as, for example, air or water, when the lumen needs to be occluded prior to insertion.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A catheter comprising:
    an elongated body defining a first lumen, a second lumen, and a septum disposed between the first and second lumens;
    a first member defining a cavity, the first member extending within the first lumen and being slidably movable relative to the first lumen; and
    a second member received within the second lumen and configured to be slidably movable relative to the second lumen,
    wherein the cavity of the first member is configured to receive the second member, wherein when the second member is within the cavity of the first member, the first and second members are configured to extend beyond a distal end of the elongated body in a tapered configuration.

2. The catheter of claim 1, wherein the first member comprises a distal portion that extends beyond the distal end of the elongated body, and wherein the distal portion defines the cavity.

3. The catheter of claim 1, wherein the first member defines a member lumen, the cavity being a portion of the member lumen.

4. The catheter of claim 1, wherein the second member includes a stylette.

5. The catheter of claim 1, wherein the second member includes a guidewire.

6. The catheter of claim 1, wherein the second member includes a stylette and a guidewire configured to extend through the stylette and the cavity.

7. The catheter of claim 6, wherein the first member includes a distal portion that extends beyond the distal end of the elongated body, the distal portion extending beyond a distal end of the stylette when the guidewire extends through the stylette and the cavity.

8. The catheter of claim 7, wherein the distal tip defines at least one rounded edge.

9. The catheter of claim 1, wherein at least a portion of at least one of the first member or the second member has a greater rigidity relative to the elongated body.

10. The catheter of claim 1, wherein a distal tip of the elongated body is comprised of a material having a durometer greater than a durometer of a more proximal portion of the elongated body.

11. The catheter of claim 1, wherein the first and second members comprise a first stylette and a second stylette, respectively, and wherein the first stylette has an outer diameter substantially equivalent to an inner diameter of the first lumen and the second stylette has an outer diameter substantially equivalent to an inner diameter of the second lumen.

12. The catheter of claim 1, wherein the cavity defined by the first member is a member lumen, the first member defining first and second openings in communication with the member lumen, the second member being insertable, from distal to proximal, into the first opening of the first member, through the member lumen, and out of the second opening of the first member, and into the second lumen of the elongated body.

13. The catheter of claim 12, wherein at least one of the first opening or the second opening is a slit defined by the elongated body.

14. The catheter of claim 1, further comprising a guidewire, wherein the first and second members comprise a first stylette and a second stylette, respectively, and wherein at least one of the first stylette or the second stylette has an inner diameter that is smaller than an outer diameter of the guidewire, and wherein when the guidewire is inserted into the at least one of the first stylette or the second stylette, the inner diameter of the at least one of the first stylette or the second stylette expands to accommodate the guidewire and when the guidewire is withdrawn from the at least one of the first stylette or the second stylette, the inner diameter contracts.

15. The catheter of claim 1, wherein the elongated body defines a third lumen configured to receive a guidewire.

16. The catheter of claim 1, wherein the elongated body defines a septum extension extending distally beyond the first and second lumens.

17. A catheter comprising:
  a catheter body defining a first lumen, a second lumen, and a septum between the first and second lumens;
  a stylette extending within the first lumen and being slidably movable relative thereto, the stylette including a distal portion configured to extend beyond a distal end of the catheter body, the distal portion of the stylette defining a member lumen; and
  an elongated member extending through the second lumen and the member lumen such that the stylette and the elongated member extend beyond the distal end of the catheter body in a tapered configuration.

18. The catheter of claim 17, wherein the elongated member comprises a guidewire.

19. The catheter of claim 17, wherein the catheter body defines a septum extension extending distally beyond the first and second lumens.

20. The catheter of claim 17, wherein a distal tip of the catheter body is comprised of a material having a durometer greater than a durometer of a more proximal portion of the catheter body.

21. The catheter of claim 17, wherein the stylette comprises a first stylette, the catheter further comprising a second stylette, wherein at least one of the first stylette or the second stylette has an inner diameter that is smaller than an outer diameter of the elongated member, and wherein when the elongated member is inserted into the at least one of the first stylette or the second stylette, the inner diameter of the at least one of the first stylette or the second stylette expands to accommodate the elongated member and when the elongated member is withdrawn from the stylette, the inner diameter contracts.

22. A method comprising:
  introducing a catheter into a patient, the catheter comprising:
    an elongated body defining a first lumen, a second lumen, and a septum disposed between the first and second lumens;
    a first member defining a cavity, the first member extending within the first lumen and being slidably movable relative to the first lumen; and
    a second member received within the second lumen and configured to be slidably movable relative to the second lumen,
    wherein the cavity of the first member is configured to receive the second member, wherein when the second member is within the cavity of the first member, the first and second members are configured to extend beyond a distal end of the elongated body in a tapered configuration;
  guiding the catheter to a target site within the patient; and
  after the catheter is guided to the target site, removing the second member from the cavity of the first member.

23. The method of claim 22, wherein the second member includes a stylette.

24. The method of claim 22, wherein the second member includes a guidewire.

* * * * *